United States Patent
Neyens

(10) Patent No.: US 7,418,882 B2
(45) Date of Patent: Sep. 2, 2008

(54) MEASURING PROBE

(75) Inventor: Guido Jacobus Neyens, Opoeteren (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 85 days.

(21) Appl. No.: 11/610,547

(22) Filed: Dec. 14, 2006

(65) Prior Publication Data
US 2007/0137286 A1 Jun. 21, 2007

(30) Foreign Application Priority Data
Dec. 15, 2005 (DE) ............... 10 2005 060 493

(51) Int. Cl.
*G01D 11/24* (2006.01)
*G01L 19/14* (2006.01)

(52) U.S. Cl. ............... 73/866.5; 73/431; 204/422; 374/139

(58) Field of Classification Search ............ 73/431, 73/866.5; 204/422, 423; 374/139, 140
See application file for complete search history.

(56) References Cited

U.S. PATENT DOCUMENTS

| | | | | |
|---|---|---|---|---|
| 3,719,574 A | * | 3/1973 | Richardson | 204/422 |
| 4,342,633 A | * | 8/1982 | Cure | 204/423 |
| 4,361,053 A | * | 11/1982 | Jones et al. | 73/864.53 |
| 4,401,389 A | * | 8/1983 | Theuwis | 374/140 |
| 4,451,350 A | * | 5/1984 | Tsuchida et al. | 204/422 |
| 4,708,783 A | * | 11/1987 | Nakamura et al. | 204/423 |
| 4,717,463 A | * | 1/1988 | Clauss | 204/422 |
| 4,830,727 A | * | 5/1989 | Sasabe et al. | 204/412 |
| 4,871,263 A | * | 10/1989 | Wilson | 374/139 |
| 4,896,549 A | * | 1/1990 | Falk | 73/864.53 |
| 4,964,736 A | * | 10/1990 | Cure et al. | 374/140 |
| 5,577,841 A | * | 11/1996 | Wall | 374/140 |
| 6,013,163 A | * | 1/2000 | Hsia et al. | 204/422 |
| 6,142,664 A | * | 11/2000 | Ikawa et al. | 374/140 |
| 6,328,867 B1 | | 12/2001 | Turkdogan | |
| 7,141,151 B2 | * | 11/2006 | Habets | 204/422 |
| 7,335,287 B2 | * | 2/2008 | Jones et al. | 204/422 |

FOREIGN PATENT DOCUMENTS

| | | |
|---|---|---|
| DE | 79 25 016 U1 | 2/1980 |
| DE | 8317643.8 U1 | 6/1984 |
| DE | 35 41 806 C1 | 2/1987 |
| DE | 29 54 228 C2 | 6/1989 |
| EP | 45535 A2 * | 2/1982 |
| EP | 0 059 222 A1 | 3/1982 |
| EP | 0 544 281 A1 | 6/1993 |
| FR | 2547656 A1 | 12/1984 |
| GB | 1 317 882 | 5/1973 |
| JP | 59107257 A * | 6/1984 |
| JP | 63191056 A * | 8/1988 |
| JP | 01153954 A * | 6/1989 |

* cited by examiner

*Primary Examiner*—David A. Rogers
(74) *Attorney, Agent, or Firm*—Panitch Schwarze Belisario & Nadel LLP

(57) ABSTRACT

A measuring probe is provided for measurement in molten metal, the probe having a measuring head arranged on an immersion end of a carrier tube. A bath contact and at least one sensor for determining a component of the molten metal are arranged on the immersion end. The bath contact, viewed in the immersion direction, has a first bath contact region with two surface areas extending parallel to the immersion direction on opposite sides of the bath contact.

11 Claims, 4 Drawing Sheets

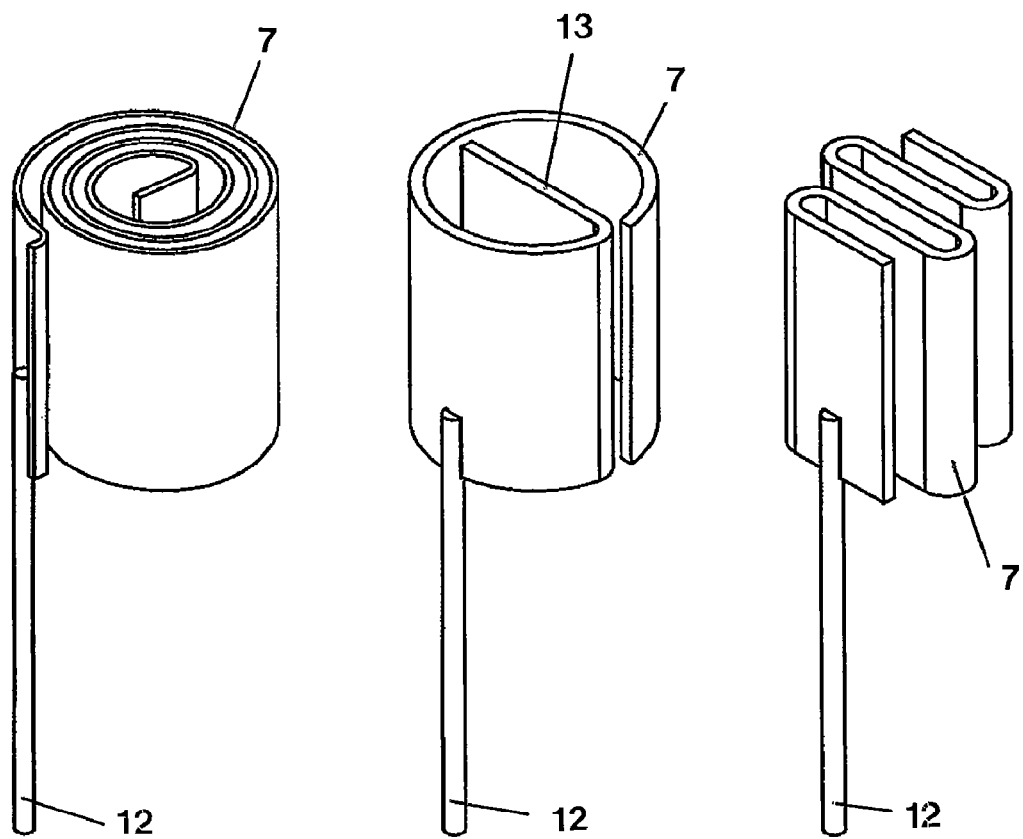
Fig. 4 aFig. 4 bFig. 4 c

MEASURING PROBE

BACKGROUND OF THE INVENTION

The invention relates to a measuring probe for measurements in metal or slag melts, the probe having a measuring head, which is arranged on an immersion end of a carrier tube and on which at least one sensor for determining a component of the molten metal and a bath contact are arranged, wherein the bath contact, viewed in the immersion direction, has a bath contact region having two surface regions parallel to the immersion direction and lying on opposite sides of the bath contact.

Such measuring probes are known in many forms. For example, in German Patent DE 3541806 C1 or in German Utility Model DE 83 17 643 U1, measuring probes are known, on whose immersion side a bath contact is arranged. The bath contact is allocated to an electrochemical measuring cell. It is constructed as a metal rod. From German Patent DE 29 54 228 C2 and German Utility Model DE 79 25 016 U1, probes are known, which have a tubular structure and which each comprise a leg of a sensor. The bath contact can also be used, in addition to the interaction with an electrochemical element, for measuring the bath level of a molten metal, for example of the type where upon immersion of the bath contact into the molten metal, a circuit is closed and the level of the molten metal is determined from the position of the bath contact. The bath contact is usually made of steel and is destroyed within the molten metal after a short time.

BRIEF SUMMARY OF THE INVENTION

An object of the present invention is to improve the known measuring probes and, in particular, the bath contact arrangements used in these probes and thus to increase the reliability of the measuring probes.

According to the invention, a measuring probe is provided for measurement in molten metal, the probe comprising a measuring head arranged on an immersion end of a carrier tube, a bath contact and at least one sensor for determining a component of the molten metal being arranged on the immersion end. The bath contact, viewed in an immersion direction, has a first bath contact region having two surface regions extending parallel to the immersion direction lying on opposite sides of the first bath contact and a second bath contact region having two surfaces regions extending parallel to the immersion direction and lying on opposite sides of the second bath contact. A material stable in molten iron or steel is arranged on the opposite surface regions of the first bath contact region, a material stable in molten iron or steel is arranged on at most only one of the opposite surface regions of the second bath contact region, and at least one of the opposite surface regions of the second bath contact region is free of the stable material.

Because a material that is stable in molten iron or steel is arranged on the opposing surface regions of the first bath contact region and a material that is stable in molten iron or steel is arranged on a second bath contact region at most one surface region, with the opposing surface region of the second bath contact region being free of this material, it is thereby assured that the surface regions of the first bath contact region are better protected from the molten metal (for example, molten steel) than at least one of the surface regions of the second bath contact. This second bath contact region is thereby more exposed to the molten metal and therefore destroyed first, i.e., before the first bath contact region.

In one embodiment of the invention, a stable material surface structure that is inclined relative to the cross section of the measuring head is constructed as an approximately conical shape to form a sort of hill or mound. The first bath contact region is arranged essentially embedded in the hill with its forward edge exposed at a forward level in the immersion direction. The second bath contact region is arranged outside the stable material surface, extending laterally (radially) and rearwardly (axially) from the first bath contact region. The surface of the stable material falls away toward the peripheral edges of the bath contact in the direction opposite to the immersion direction. Gas bubbles, which form at the front side of the bath contact upon immersion, cannot collect there, but instead they are led away laterally rearwardly, so that the contact between the molten steel and the bath contact is not destroyed or interfered with by the bubbles.

Preferably, the bath contact extends, in the immersion direction, in front of the outer surface of the measuring head. The two-sided arrangement of the stable material extends expediently from the first bath contact region up to the measuring head. In addition, the second bath contact region and the first bath contact region are expediently arranged laterally adjacent to each other in a projection plane arranged perpendicular to the immersion direction. The first bath contact region is preferably arranged in the immersion direction such that its forward edge is at least 3 mm in front of the front surface of the measuring head, in order to better lead away the gas, because at this minimum distance, the slope/drop-off is sufficiently large.

The bath contact can be formed of a metal sheet. It can also be formed of a metal rod, for example as mentioned in the prior art described above, wherein then the stable material has an asymmetric arrangement around the metal rod. In this way, a first and a second bath contact region are also formed thereby. For the second bath contact region, it is important that the bath contact itself is not so well protected there from the molten metal (molten iron or steel) as the first bath contact region, so that it dissolves faster in the second region, while forming the described hill-like structure.

It is further advantageous that the bath contact formed, in particular from a metal sheet, is bent about an axis approximately parallel to the immersion direction, whereby a portion of the metal sheet is arranged within the silhouette formed by the bend. The stable material preferably fills up the silhouette and exposes portions of the bath contact on the outer periphery. Preferably, foundry sand or cement is used as the stable material.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIGS. 4a, 4b and 4c are perspective views of various embodiments of bath contacts not yet assembled into the measuring head.

DETAILED DESCRIPTION OF THE INVENTION

Figure 1:
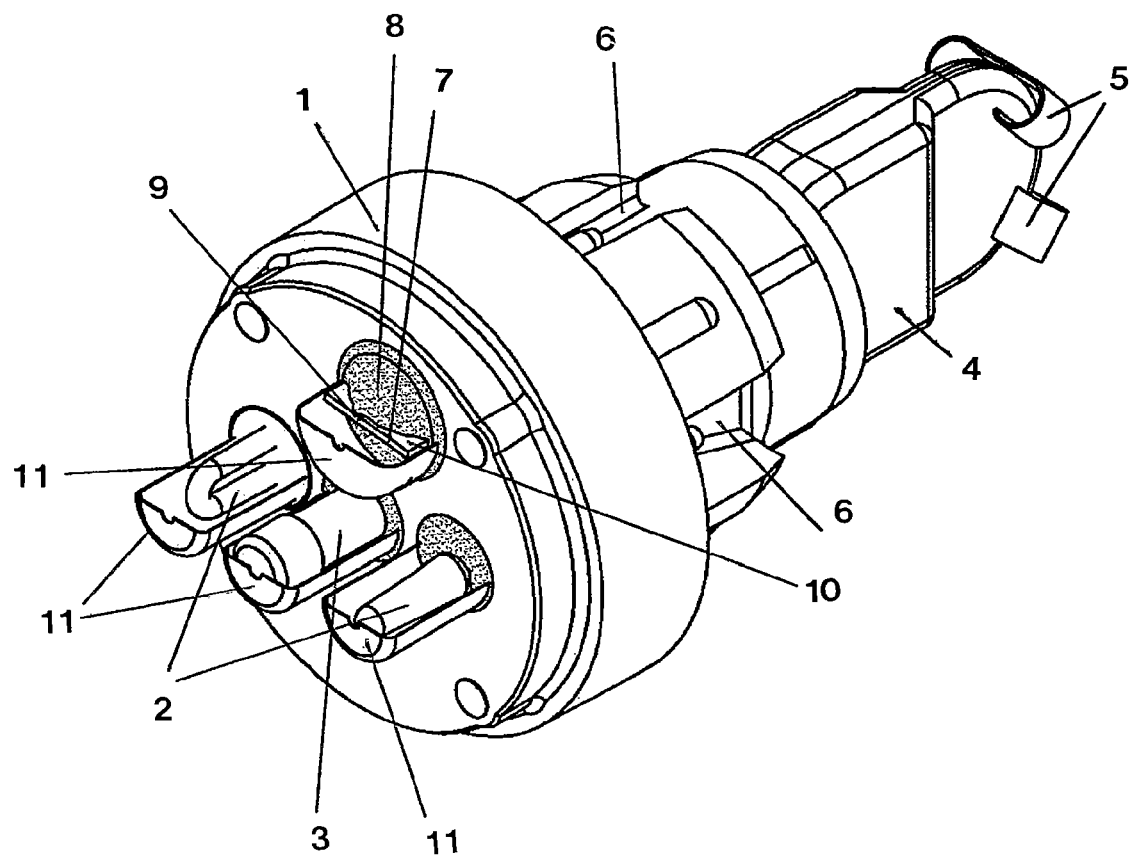
FIG. 1 is a perspective view, partially broken away, of the front (immersion) end of the measuring head of a sample measuring probe of the invention, showing one embodiment of the bath contact.

FIG. 1 shows the measuring head 1 of a sample measuring probe. Sensors 2 and also the inlet tube 3 of a sample chamber 4, located on the rear end of the measuring head 1, are arranged on the immersion end of the measuring head. The sample chamber 4 is a typical two-shell sample chamber, which is held together at its end with clamps 5. A carrier tube (not shown in the drawing) is placed on the rear end of the measuring head 1. Recesses 6 for contacting the rear-side connections of the sensors 2 can be seen on the measuring head 1. In addition, a bath contact 7 is arranged on the immersion end of the measuring head 1.

In the embodiment of FIG. 1 the bath contact 7 has the shape of an approximately flat metal sheet. It is embedded in refractory cement 8 and is surrounded by cement 8 in its first bath contact region 9 (approximately in the middle) up to its forward end edge. The second bath contact region 10, here formed as two flaps or ears extending laterally from the stable material and rearwardly from the front edge of the bath contact 7, is relatively unprotected from the molten steel when it is immersed; it is melted off. The conical shape of the cement 8 shown in FIG. 1 allows the discharge of gases from the region of the front end edge of the bath contact 7 by sliding over the rearwardly and outwardly sloping surface of the cone or hill, so that a faultless contacting with the molten steel is possible. The bath contact 7, the sensors 2, and the inlet tube 3 are surrounded by protective caps 11.

Figure 2:
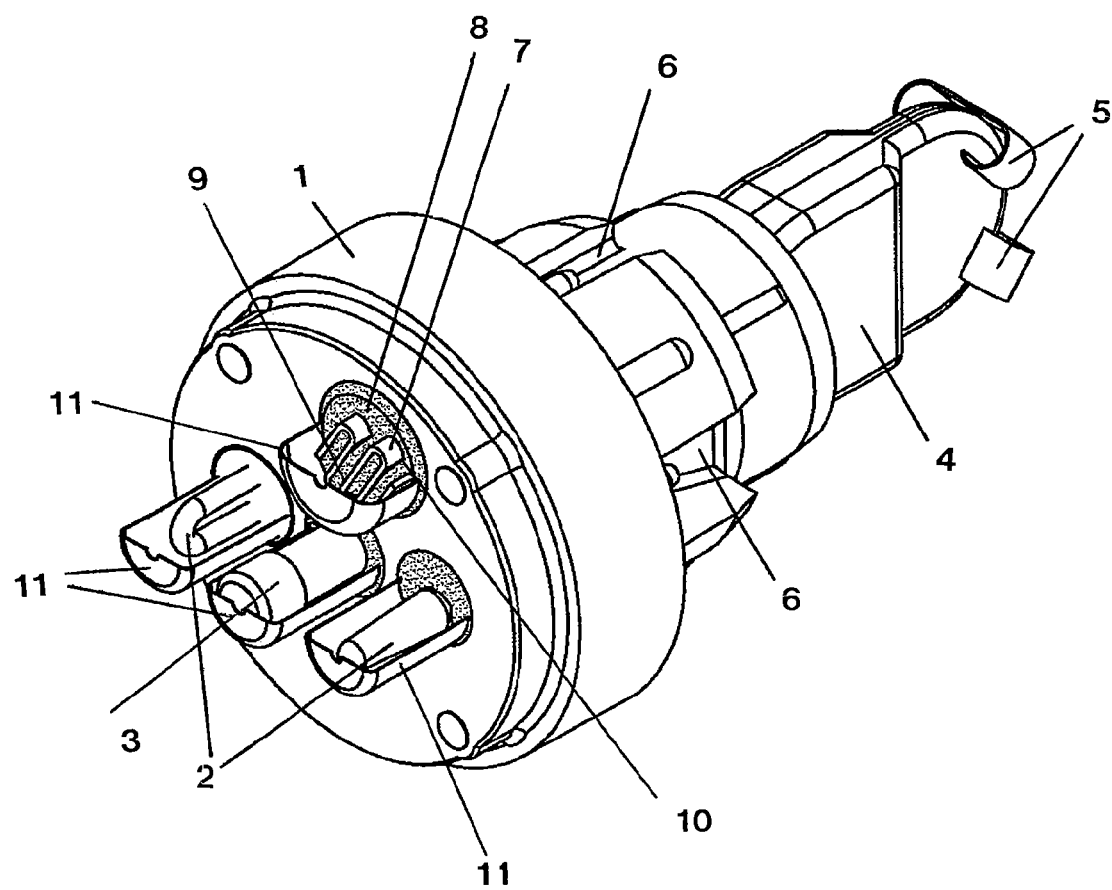
FIG. 2 is a perspective view similar to FIG. 1, showing a measuring head of a sample measuring probe according to the invention, having another embodiment of a bath contact.

In FIG. 2 a similar measuring head 1 is shown. In contrast to the embodiment according to FIG. 1, the bath contact 7 shown in FIG. 2 has a meander-shaped structure with a first bath contact region approximately in the center of the bath contact 7 and a second bath contact region on the outer periphery. Such a bath contact is shown in FIG. 4c. It is connected through a bore in the measuring head 1 to a contact line by means of a contact 12 in a recess 6. Here, since the second bath contact region is only protected by the stable material on its inner surface, the outer surface region is exposed to the molten metal and melts away upon immersion, so that a hill or mound is provided by the central first bath contact region and stable material surrounding it. Again, this structure facilitates the leading away of the gases in the belt rearwarly to prevent accumulation of gases at the front end of the bath contact and resulting interference with the contact between the molten metal and the first bath contact region.

Figure 3:
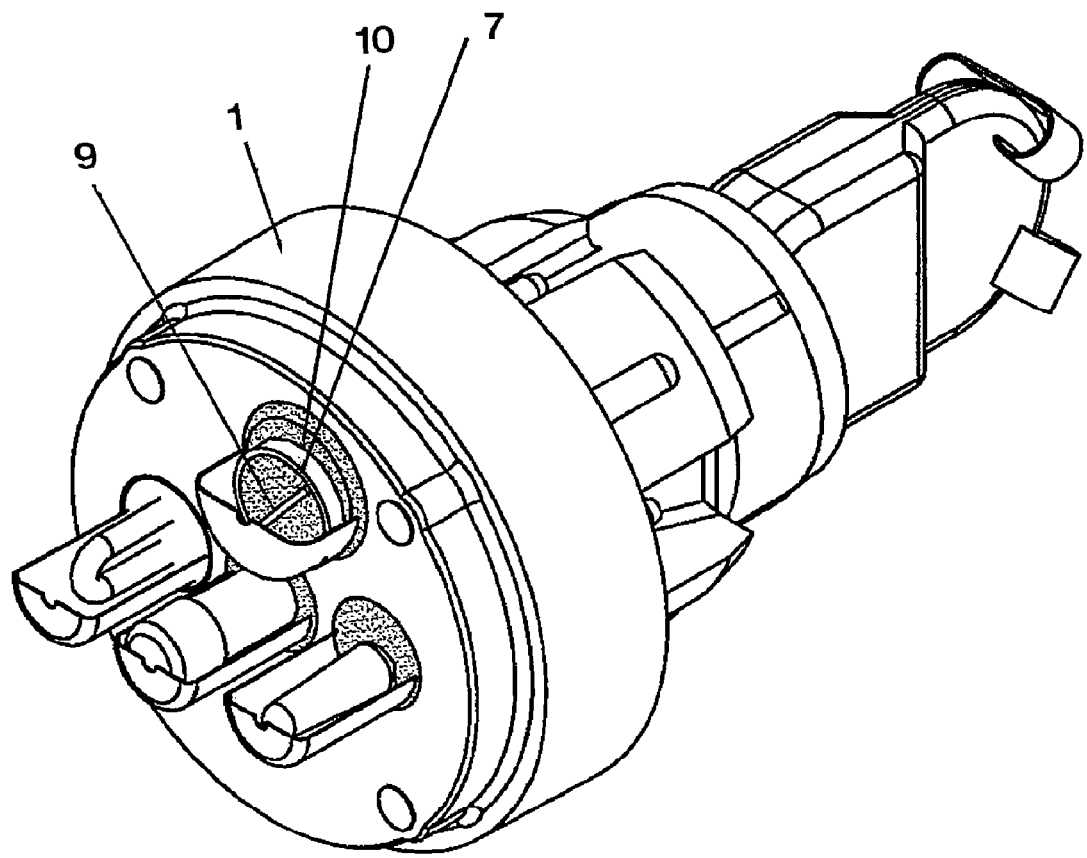
FIG. 3 is a perspective view similar to FIGS. 1 and 2, showing a measuring head of a sample measuring probe according to the invention, having another embodiment of a bath contact.

FIG. 3 shows another embodiment of a bath contact 7, with the same construction of the measuring head 1. The bath contact 7 is constructed as a metal sheet bent into a circle, whose one end 13 is bent into the inside of the circle (see FIG. 4b). The contacting is realized in the same manner in all of the shown embodiments. The first bath contact region 9 is located approximately in the center of the circle formed by the bath contact 7, while the second bath contact region 10 is located on the outer periphery. The interior of the circle is filled up completely or nearly completely with foundry sand or cement. Here again, exposure of the outer surface region of the second bath contact region 10 results in its melting first upon contact with the molten metal, leaving the first bath contact region 9 in the center surrounded by the stable material, so that gas bubbles slide rearwarly over the outer edges of the stable material to allow non-interfering contact of the molten metal with the first bath contact region.

While the embodiments shown in FIGS. 1-3, have the first bath contact region in the center and the second bath contact region extending radially toward the outer periphery, it will be understood, the first bath contact region could be on the periphery and the second bath contact region toward the center. However, since the second bath contact region is always less protected by the stable material, contact with the molten metal will in this case melt away the central area to form a concavity hole into which the gas bubbles may flow away from the front edge of the bath contact to allow adequate contact with the molten metal. Other formations of the first and second bath contacts will suggest themselves to persons of ordinary skill in the art based upon the above disclosure.

FIG. 4a shows another embodiment of the bath contact 7. Here, in contrast to the embodiment shown in FIG. 4b, not only is a flat surface bent into the circle interior, but the sheet is also wound into the shape of a spiral spring.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A measuring probe for measurement in molten metal, the probe comprising a measuring head arranged on an immersion end of a carrier tube, a bath contact and at least one sensor for determining a component of the molten metal being arranged on the immersion end, wherein the bath contact, viewed in an immersion direction, has a first bath contact region having two surface regions extending parallel to the immersion direction lying on opposite sides of the first bath contact and a second bath contact region having two surfaces regions extending parallel to the immersion direction and lying on opposite sides of the second bath contact, wherein a material stable in the molten metal is arranged on the opposite surface regions of the first bath contact region, wherein a material stable in the molten metal is arranged on at most only one of the opposite surface regions of the second bath contact region, and wherein at least one of the opposite surface regions of the second bath contact region is free of the stable material.

2. The measuring probe according to claim 1, wherein the bath contact extends in the immersion direction in front of an outer surface of the measuring head.

3. The measuring probe according to claim 1, wherein the arrangement of the stable material on the opposite surface regions of the first bath contact region extends from approximately adjacent a front edge of the first bath contact region back to a front surface of the measuring head.

4. The measuring probe according to claim 1, wherein the second bath contact region and the first bath contact region are arranged laterally adjacent each other in a projection plane arranged perpendicular to the immersion direction.

5. The measuring probe according to claim 1, wherein a front edge of the first bath contact region is arranged in the immersion direction at least 3 mm in front of a front surface of the measuring head.

6. The measuring probe according to claim 1, wherein the stable material is foundry sand or cement.

7. The measuring probe according to claim 1, wherein the stable material has an outer surface shaped in such a way as to lead gas bubbles in the molten metal away from exposed surface regions of the first bath contact region.

8. The measuring probe according to claim 1, wherein the second bath contact region is consumed first by contact with the molten metal, such that gas bubbles in the molten metal may be led away from a front edge of the first bath contact region along a thus exposed outer surface of the stable material.

9. The measuring probe according to claim 1, wherein the bath contact comprises a metal sheet.

10. The measuring probe according to claim 9, wherein the bath contact is bent around an axis approximately parallel to the immersion direction, and wherein one portion of the metal sheet is arranged within a silhouette formed by the bend.

11. The measuring probe according to claim 10, wherein the stable material fills up the silhouette.

* * * * *